United States Patent [19]

Chang et al.

[11] Patent Number: 4,472,535
[45] Date of Patent: Sep. 18, 1984

[54] CONVERSION OF SYNTHESIS GAS TO ETHANE

[75] Inventors: Clarence D. Chang, Princeton; Richard F. Socha, Trenton, both of N.J.

[73] Assignee: Mobil Oil Corporation, New York, N.Y.

[21] Appl. No.: 443,499

[22] Filed: Nov. 22, 1982

[51] Int. Cl.³ .............................................. C07L 1/04
[52] U.S. Cl. ................................... 518/714; 518/713; 518/715; 518/728; 502/73; 502/77
[58] Field of Search ................ 518/713, 714, 715, 728

[56] References Cited

U.S. PATENT DOCUMENTS

| 4,096,163 | 6/1978 | Chang et al. | 518/714 |
|---|---|---|---|
| 4,157,338 | 6/1979 | Haag et al. | 518/715 |
| 4,172,843 | 10/1979 | Dwyer et al. | 518/715 |
| 4,177,202 | 12/1978 | Chang et al. | 518/714 |
| 4,188,336 | 2/1980 | Chang et al. | 518/714 |
| 4,255,349 | 3/1981 | Butter et al. | 518/719 |
| 4,403,044 | 9/1983 | Post et al. | 518/714 |

FOREIGN PATENT DOCUMENTS 2518097  11/1975  Fed. Rep. of Germany ...... 518/714

*Primary Examiner*—Howard T. Mars
*Attorney, Agent, or Firm*—Alexander J. McKillop; Michael G. Gilman; Laurence P. Hobbes

[57] ABSTRACT

Synthesis gas is converted to an exclusively hydrocarbon product with selectivity to ethane by the use of a catalyst which comprises a zeolite and a metal component distributed within the pore structure of the zeolite. The preferred zeolites have a Constraint Index of 1 to 12 and a silica:alumina ratio of at least 12:1 and of these ZSM-5 is preferred. The metal component which may be introduced into the zeolite by impregnation from liquid ammonia solutions, is preferably chromium, zinc and aluminum, optionally with potassium.

27 Claims, No Drawings

CONVERSION OF SYNTHESIS GAS TO ETHANE

FIELD OF THE INVENTION

The present invention is directed to the conversion of synthesis gas to ethane by a process employing a novel conversion catalyst.

BACKGROUND OF THE INVENTION

Processes for the conversion of synthesis gas, a mixture comprising carbon monoxide and hydrogen, into hydrocarbons have been known for some time, of which the Fischer-Tropsch process is a well known example. A description of the process may be found, for example, in Kirk Othmer: Encyclopedia of Chemical Technology, 3rd Edition, Vol. 11, pages 473–478 (John Wiley & Sons, New York, N.Y. 1980). In the Fischer-Tropsch process the synthesis gas is passed over a metal oxide catalyst at elevated temperatures and pressures, typically in the range of 250° C. to 500° C. (about 480° F. to 930° F.) and 1000 to 30,000 kPa (about 130 to 4340 psig); the catalyst is usually derived from a metal such as iron, cobalt, nickel or thorium. The product of the Fischer-Tropsch process is typically a mixture of hydrocarbons whose composition depends upon the nature of the catalyst employed and the selected process conditions.

Other catalysts for converting synthesis gas into hydrocarbons have also been proposed in the past. For example, U.S. Pat. No. 4,207,248 discloses a catalyst comprising a mixture of a Fischer-Tropsch component and a zeolite such as ZSM-5. U.S. Pat. Nos. 4,207,250, 4,255,349 and 4,298,695 describe the use of catalysts comprising iron, an acidic zeolite such as ZSM-5 and a matrix, with all three components combined in individual particles of the catalyst. U.S. Pat. No. 4,207,248 discloses a similar catalyst which employs cobalt instead of iron.

Proposals have been made for increasing the proportionate yield of certain kinds of hydrocarbons in the product. For example, U.S. Pat. No. 4,279,830 refers to the possibility of obtaining an improved yield of aromatics by using a iron catalyst promoted with potassium in combination with zeolite ZSM-5. The cobalt-containing catalyst of U.S. Pat. No. 4,207,248 mentioned above, is said to produce an improved yield of olefins, with a proportionately reduced yield of lower hydrocarbons such as methane and ethane. Similarly, the processes of U.S. Pat. Nos. 4,207,250, 4,255,349 and 4,208,695 are said to produce good yields of their desired higher molecular weight products while minimizing the yields of methane and other low molecular weight hydrocarbons. On the other hand, the process described in U.S. Pat. No. 4,177,202 employs a transition metal catalyst which is selective to a certain degree for the production of light gases rich in methane and ethane. The highest reported yield of ethane is 44 percent of the total hydrocarbon product and although this figure is encouraging it falls short of the amount which would be desirable in such a process.

SUMMARY OF THE INVENTION

We have now found catalysts which exhibit a remarkably high selectivity for the conversion of synthesis gas into ethane; the selectivity readily exceeds 50 percent with respect to the total hydrocarbon product and may, in fact, be higher than 70 percent or even more in favorable cases. This high selectivity is even more remarkable when it is also borne in mind that it is achieved at reasonable conversion levels. The process may be used as the first stage of a two-stage process for converting synthesis gas to ethylene, a valuable chemical product. The second stage of the process, the conversion of the ethane to ethylene, may take place by conventional pyrolysis techniques as described, for example, in Kirk-Othmer, Encyclopedia of Chemical Technology, op cit, Vol. 9, pages 400–411.

According to the present invention the synthesis gas conversion catalyst comprises a zeolite component which is preferably a crystalline zeolite having a silica:alumina ratio of at least 12:1 and a Constraint Index of 1 to 12, and a metal component which is distributed within the pores of the zeolite. The metal or metals which may be used are those which are suitable for the synthesis of alcohols from synthesis gas and a preferred metal component comprises the metals chromium, zinc and aluminum, optionally with potassium. The metal component may be deposited on the zeolite in the desired manner by impregnation using a solution of the metal salts in ammonia, as will be described below.

The conversion process of the present invention comprises contacting synthesis gas with the conversion catalyst under conversion conditions of elevated temperature and pressure, typically at temperatures from 300° C. to 500° C. (about 570° F. to 930° F.) and pressures from 10 to 1000 Atm (980 to 98,000 kPa). During the conversion, the oxygen from the synthesis gas is rejected as carbon dioxide and because of the stoichiometry of the reaction, hydrogen-lean synthesis gas (hydrogen: carbon monoxide molar ratio less than 1:1) is preferred.

DESCRIPTION OF PREFERRED EMBODIMENTS

Catalyst

The catalyst has two essential components, a zeolite component and a metal component. The metal component may be based on a single metal or, alternatively, two or more metals. In order to obtain the desired synthetic selectivity it has been found that the metal component should be distributed principally within the internal pore structure of the zeolite, suitably by means of the impregnation procedure described below.

Zeolite Component

The zeolite component comprises a crystalline zeolite which provides acidic functionality. A number of zeolites of this kind are known. They have a three-dimensional crystal structure formed of $SiO_4$ and $AlO_4$ tetrahedra crosslinked by the sharing of oxygen atoms with the resultant negative charge of the aluminum atoms which may be present balanced by a cationic component. The ratio between the silica and aluminum atoms may vary widely from the specified minimum upwards; indeed, zeolites may be brought into existence from reaction mixtures from which aluminum is excluded.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed.

Zeolites have a crystal structure which is capable of regulating the access to an egress from the intracrystalline free space. This control, which is effected by the crystal structure itself, is dependent both upon the molecular configuration of the material which is or, alternatively, is not, to have access to the internal structure of the zeolite and also upon the structure of the zeolite itself. The pores of the zeolite are in the form of rings which are formed by the regular disposition of the tetrahedra making up the anionic framework of the crystalline aluminosilicate, the oxygen atoms themselves being bonded to the silicon or aluminum atoms at the centers of the tetrahedra. A convenient measure of the extent to which a zeolite provides this control for molecules of varying sizes to its internal structure is provided by the Constraint Index of the zeolite: zeolites which provide but highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,177,202 to which reference is made for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by artifices including base exchange, steaming or control of silica:alumina ratio.

Divers zeolites may be used in the catalysts of the present invention. Upon a classification based upon the pore size of the zeolites, the zeolites which may be used include small pore, large pore and intermediate pore size zeolites, of which the latter are frequently preferred. Exemplary small pore zeolites (i.e. zeolites having a pore size which is effectively equivalent to that provided by an 8 membered ring of oxygen atoms) include zeolite A, erionite and ZSM-34. Exemplary large pore zeolites (i.e. zeolites having a pore size of at least 6 A°, effectively equivalent to that provided by a 12-membered ring of oxygen atoms) include zeolite Y (including Ultrastable Y), mordenite, zeolite beta and zeolites ZSM-4 and ZSM-20. The so-called intermediate pore size zeolites which have a pore size effectively equivalent to that of a 10-membered ring of oxygen atoms are most easily characterized by a Constraint Index of 1 to 12 (see above) and a silica:alumina ratio of at least 12:1, generally above 30:1. Zeolites of this kind include ZSM-5, ZSM-11, the ZSM-5/ZSM-11 intermediate, ZSM-12, ZSM-23, ZSM-35 and ZSM-38, of which ZSM-5 is preferred. Zeolite ZSM-4 is described in U.S. Pat. No. 3,923,639, ZSM-20 in U.S. Pat. No., 3,972,983, ZSM-34 in U.S. Pat. No. 4,086,186 and zeolite beta in U.S. Pat. No. 3,308,069 and Re. 28,341, to which reference is made for details of these zeolites, their preparation and properties. The preferred zeolites which have a Constraint Index of 1–12 and a silica:alumina ratio of at least 12:1 are described in U.S. Pat. Nos. 3,702,886 (ZSM-5), 3,709,979 (ZSM-11), 3,832,449 (ZSM-12), 4,076,842 (ZSM-23), 4,016,245 (ZSM-35), 4,046,859 (ZSM-38) and 4,229,424 (ZSM-5/ZSM-11 intermediate) and reference is made to these patents for details of these zeolites, their preparation and properties. More highly siliceous forms of ZSM-5 are described in U.S. Pat. No. Re. 29,948 and of ZSM-11 and ZSM-12 in European Patent Publication Nos. 14,059 and 13,630, respectively, to which reference is also made for details of those forms, their preparation and properties.

The zeolite should be at least partly in the hydrogen form in order to provide the acidic functionality which is required in the conversion process. The zeolite may be activated and brought into the hydrogen form subsequent to its synthesis from a solution containing organic cations by the activation procedure described in U.S. Pat. No. 4,177,202 to which reference is made for details of the procedure. Briefly, the activation procedure used for zeolites prepared in the presence of organic cations comprises calcining the zeolite e.g. in an inert atmosphere for at least one hour at 500° C., to decompose the organic material, followed by base exchange with ammonium salts, followed by calcination e.g. in air at 500° C. for at least one hour.

The zeolite may be incorporated into a matrix which is resistant to the temperatures and other conditions encountered in the conversion process. Suitable matrix materials such as clays, silica and other oxides such as alumina and silica-alumina are described in U.S. Pat. No. 4,016,218 to which reference is made for details of such matrix materials.

Metal Component

The metal component may be derived from one or more metals. Suitable metals are those which may be used for the synthesis of alcohols from synthesis gas, especially those which are used for the synthesis of methanol or ethanol from synthesis gas. Since the principal commercial alcohol synthesis is of methanol, the metal component may be regarded as a methanol synthesis component. Components which are suitable for use may therefore be based on the metals palladium, thorium, platinum, iridium, copper, manganese, cobalt, chromium, zinc, rhodium and aluminum. Combinations of metals such as platinum-iridium, copper-manganese, copper-cobalt, copper-zinc, copper-chromium-zinc, zinc-chromium, rhodium-aluminum are normally particularly useful and a preferred combination is of the metals chromium, zinc, aluminum and, optionally, potassium.

For the preferred combination of chromium, zinc, aluminum and optionally, potassium, the atomic ratios in which these metals will normally be present is 0.1–10:0.1–10:0.1–10:0–10 (Cr:Zn:Al:K), referred to each aluminum atom in the zeolite preferably, the ratio will be 0.5–2.0:0.5–2.0:0.5–2.0:0–2.0, on the same basis. Generally, this will be equivalent to a loading of 0.1 to 50, preferably 1 to 20, weight percent of the metal components, calculated as the oxides, based on the total weight of the active catalyst components (zeolite+metal). As an example, a ZSM-5 (70:1 silica:alumina) loaded with a Cr/Zn/Al metal component at a 1:1:1:1 atomic ratio (1:1:1 Cr:Zn:Al relative to each Al atom of the zeolite) contains 91.2% ZSM-5, 2.2% Al$_2$O$_3$, 3.2% Cr$_2$O$_3$ and 3.4% ZnO, calculated on an oxide basis.

Other metal components may be used in the ratios in which they are suitable for catalyzing the conversion of synthesis gas to alcohols, especially methanol, although in this case the desired product will be hydrocarbon, with a selectivity to ethane.

In order to maximize the desired conversion to ethane the metal component of the catalyst should be disposed within the intracrystalline pore structure of the zeolite. This may be achieved by impregnating the metal into the zeolite using an ammoniacal solution of a compound of the metal, i.e. a solution of a compound of the metal in liquid ammonia or concentrated aqueous ammonia. The impregnation is suitably carried out by dissolving precursors of the metal component (which may be referred to as a multimetallite) in an ammonia solvent and then contacting the zeolite with the solution. The ammonia solvent which is used may be liquid ammonia or aqueous ammonia containing greater than 50 weight percent ammonia. Prior to impregnation with the solution, the zeolite should, if necessary, be calcined in an inert atmosphere to drive off any organic cations which remain after formation of the zeolite and which would otherwise tend to block the pore structure of the zeolite.

The metal compounds which may be used as precursors for the metal component include the chlorides and nitrates as well as ammonium metal oxides. The preferred salts are the nitrates, e.g. hydrated nitrates such as Zn(NO$_3$)$_2$.gH$_2$O, Al(NO$_3$)$_3$.9H$_2$O, Cr(NO$_3$)$_3$.9H$_2$O. Oxides such as molybdenum oxide MoO$_3$ or chlorides such as gallium chloride GaCl$_3$ may be used for metal components which include such metals. Other suitable multimetalite precursors include the metal amine heteropoly salts described in U.S. Pat. No. 3,752,776 to which reference is made for details of these salts.

If desired, the metal or metals may be impregnated into the zeolite by addition of the ammonia solvent to a mixture of the zeolite and the precursor or precursors of the metal component. Addition of the ammonia solvent dissolves the metal compound or compounds and the resulting solution then permeates the zeolite to impregnate the metal component into the pore structure of the zeolite. Another alternative procedure which may be used with metal components comprising a number of metals is to impregnate each metal compound separately into the zeolite and to calcine as described below after each individual impregnation.

After impregnation, the zeolite is dried, generally under mild conditions, to drive off the solvent and fix the metal component on the zeolite. Temperatures of up to 200° C., preferably 110° to 130° C. are suitable for this purpose. The resulting dried composition is then calcined, suitably at temperatures of 250° to 650° C., preferably 300° to 500° C., to convert the precursors to the final desired form. Calcination may be continued for 0.5 to 24 hours, but in most cases a duration of 1 to 4 hours will be satisfactory. Calcination is preferably carried out in an inert atmosphere such as nitrogen or helium although air calcination may also be used, particularly at lower temperatures.

A method for producing zeolites containing occluded multimetalites using an ammoniacal impregnant is described in U.S. patent application Ser. No. 425,361, filed Sept. 28, 1982 of J. N. Miale, P. D. Perkins and C. D. Chang entitled "Zeolite containing Occluded Multimetalite", to which reference is made for details of the method.

Following calcination, the catalyst is suitably pretreated in hydrogen at elevated temperature prior to use. It is preferred to use hydrogen diluted by an inert gas such as nitrogen or helium, with treatment temperatures of 150° C. to 300° C. (300° F. to about 570° F.) being recommended. The catalyst should not, at this stage, be subjected to a severely reducing atmosphere if maximum activity and selectivity is to be retained. A diluted hydrogen atmosphere, e.g. up to 10% hydrogen in helium, is therefore to be recommended.

The catalyst may be oxidatively regenerated following use by treatment at an elevated temperature in an oxidizing atmosphere e.g. at a temperature of at least 150° C., usually 250° C. to 500° C. in air or oxygen for at least 1 hour.

Synthesis Gas Conversion

Synthesis gas, comprising carbon monoxide and hydrogen with a certain proportion of carbon dioxide, depending upon the source of the gas may be obtained in the conventional manner from a suitable gasifier e.g. a Lurgi gasifier, as described in Kirk-Othmer, Synthetic Fuels, *op cit.* The reaction which takes place during the conversion may be represented by the equation:

$$4CO + 3H_2 = CH_3-CH_3 + 2CO_2$$

The stoichiometric ratio of the hydrogen to the carbon monoxide is therefore 0.75:1, indicating a preference for low ratio synthesis gas. Because such low ratio gas is readily produced by modern, high efficiency gasifiers, the conversion process may be readily operated at high efficiency with respect to the raw materials used in the production of the synthesis gas. If the synthesis gas which is available has a hydrogen:carbon monoxide ratio below the stoichiometric 0.75:1, the amount of hydrogen may be increased by making use of the water gas shift reaction:

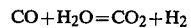

$$CO + H_2O = CO_2 + H_2$$

In practice, the water gas shift is achieved by increasing the amount of steam fed to the gasifier; the carbon dioxide formed in the reaction may be removed by scrubbing but this is not essential because, as mentioned previously, carbon dioxide is a by-product of the conversion and is inevitably present. Alternatively, any hydrogen deficiency in the synthesis gas may be cured by injecting steam into the conversion reactor where the water gas shift will take place although this will not normally be preferred because the zeolite component of the catalyst will undergo accelerated aging in the presence of the increased amounts of water.

The effluent from the conversion reaction, containing relatively high amounts of carbon dioxide may be recycled after scrubbing to remove the carbon dioxide or, alternatively, it may be used in a Fischer-Tropsch conversion in which the presence of the carbon dioxide may be utilized.

The conversion is carried out by passing the synthesis gas in contact with the catalyst under conversion conditions of elevated temperature and pressure. Temperatures of 200° C. to 650° C. (about 390° F. to 1200° F.), typically 300° C. to 500° C. (about 570° F. to 930° F.) will normally be used. High pressures of at least 10 Atm. up to 1000 Atm. (980 to 98,000 kPa), generally in the range 50 to 500 Atm. (4900 to 49,000 kPa) are normally used with high flow rates of 10 to 5000 GHSV, normally 100 to 1000 GHSV. Under these conditions, conversions over 10 percent relative to the carbon monoxide are usually obtained and in most cases the conversion will be over 30 percent. The selectivity to ethane is usually at least 50 percent and may be higher than 80 percent in favorable cases.

The conversion of the hydrogen and carbon monoxide in the synthesis gas is dependent upon the temperature at which the conversion is carried out, increasing with increasing temperature. The selectivity to the production of ethane, on the other hand, tends to decrease with increasing temperature but the observed decrease in ethane selectivity is accounted for by an increase in methane production as the proportion of ethane in the $C_{2+}$ hydrocarbon product remains almost constant, with only a slight decrease at higher temperatures. The relationships between temperature and conversion on the one hand and temperature and selectivity on the other indicate that there is an optimum temperature range with which the best balance of conversion and selectivity may be attained. Although this range may vary somewhat with the precise nature of the catalyst and the other conversion conditions employed, the optimal temperature range is from 350° C. to 500° C. (about 650° F. to 930° F.), with a preferred range of 375° C. to 475° C. (about 700° F. to 890° F.). Within these ranges, conversion and selectivity will each generally be at least 25 percent by weight (CO conversion) and in the preferred optimal range, both may be expected to exceed 40 percent or an even higher figure.

The conversion may take place in fixed bed, moving bed, ebullating bed or fluidized bed reactors. The effluent from the reactor may be recycled, as described above, with or without scrubbing to remove carbon dioxide or it may be passed to a Fischer-Tropsch conversion for recovery of the carbon values in the carbon dioxide.

The invention is illustrated by the following Examples in which all parts, proportions and percentages are by weight unless the contrary is so stated.

EXAMPLES 1–4

Four catalysts were prepared by dissolving the nitrates of the impregnant metals in liquid ammonia in the amounts appropriate to the desired catalyst loading and mixing a zeolite with the liquid ammonia solution. Evaporation of the ammonia was then permitted, to form the impregnated zeolite catalysts having the identities set out in Table 1 below.

The impregnated catalysts were calcined in air at 540° C. and then pre-treated in dilute hydrogen (0–8.5% $H_2$ in He) at 205° C. prior to use. The alpha values of the catalysts so produced are also shown in Table 1.

TABLE 1

| | Syngas Conversion Catalysts | | | |
|---|---|---|---|---|
| Example | Catalyst | | Zeolite $SiO_2/Al_2O_3$ | Alpha |
| 1 | 1:1:1 | Cr:Zn:Al:ZSM-5 | 70:1 | 900 |
| 2 | 2:2:2:1 | Cr:Zn:Al:ZSM-5 | 70:1 | 370 |
| 3 | 1:1:1:1 | K:Cr:Zn:Al:ZSM-5 | 70:1 | 30 |
| 4 | 1:1:1:1 | Cr:Zn:Al:ZSM-5 | 26000:1 | — |

The constitutions of the catalysts are reported as the atomic ratios of the metals to each atom of aluminum in the zeolite. For the 26000:1 ratio ZSM-5, the metal ratios were calculated as if the zeolite had a 70:1 silica:alumina ratio.

EXAMPLE 5

The catalyst of Example 1 was used in the conversion of synthesis gas by passing a 2:1 mixture of hydrogen and carbon monoxide over the catalyst under the conditions shown in Table 2 below, at a constant pressure of 10170 kPa (1460 psig).

The only conversion products obtained were light paraffins and carbon dioxide; no oxygenates or olefins were found and only a small amount of water was formed. The conversion and selectivity figures obtained are shown in Table 2 below.

TABLE 2

| Synthesis Gas Conversion to Ethane | | | | | | | | | |
|---|---|---|---|---|---|---|---|---|---|
| TOS (days) | 0.1 | 2.8 | 3.0 | 5.8 | 6.0 | 6.8 | 7.0 | 7.1 | 7.5 |
| GHSV | 500 | 500 | 500 | 500 | 500 | 500 | 500 | 250 | 500 |
| Temperature (°C.) | 345 | 400 | 425 | 370 | 425 | 455 | 480 | 370 | 370 |
| Conversion (%) | | | | | | | | | |
| $H_2$ | 4 | 12 | 22 | 10 | 19 | 33 | 51 | 4 | 1 |
| CO | 11 | 27 | 39 | 15 | 46 | 61 | 75 | 14 | 12 |
| Selectivity (Wt. % of organics) | | | | | | | | | |
| $CH_4$ | 5 | 10 | 17 | 12 | 22 | 33 | 56 | 51 | 35 |
| $C_2H_6$ | 83 | 83 | 74 | 81 | 69 | 58 | 39 | 43 | 45 |
| $C_3H_8$ | 7 | 4 | 6 | 3 | 6 | 7 | 5 | 4 | 17 |
| $C_4H_{10}$ | 5 | 3 | 3 | 3 | 3 | 2 | 1 | 3 | 4 |

The results given in Table 2 above show a high selectivity to ethane at reasonable conversion levels. The conversion increases as temperature increases but at the expense of ethane selectivity, mainly because of an increase in the amount of methane formed since the amount of ethane in the $C_{2+}$ hydrocarbons was found to remain substantially constant over the temperature range employed.

In an extended aging run conducted over a 19 days period at 370° C., 10170 kPa, 500 GHSV, the CO conversion decreased from 27 to 22% while the ethane selectivity remained between 65 and 70%, indicating good catalyst stability.

EXAMPLE 6

The effects of varying the catalyst composition were investigated by using the catalysts of Examples 1, 2, and 3 in the conversion of the 2:1 hydrogen:carbon monoxide synthesis gas at a pressure of 10170 kPa (1460 psig).

The conditions used and results obtained are shown in Table 3 below.

TABLE 3

| | Effect of Catalyst Composition | | | |
|---|---|---|---|---|
| Catalyst: | Ex. 1 | Ex. 1 | Ex. 2 | Ex. 3 |
| Metal Comp. | CrZnAl | CrZnAl | $Cr_2Zn_2Al_2$ | KCrZnAl |
| Alpha | 900 | 900 | 370 | 30 |
| TOS (days) | 2.8 | 5.8 | 2.0 | 0.9 |
| Temperature (°C.) | 400 | 370 | 400 | 370 |
| Conversion (%) | | | | |
| $H_2$ | 12 | 10 | 19 | 9 |
| CO | 27 | 15 | 39 | 10 |
| Selectivity (Wt. % of organics) | | | | |
| $CH_4$ | 10 | 12 | 11 | 11 |
| $C_2H_6$ | 83 | 81 | 75 | 74 |
| $C_3H_8$ | 4 | 3 | 7 | 6 |
| $C_4H_{10}$ | 3 | 3 | 5 | 8 |
| $C_5H_{12}$ | 0 | 0 | tr | 0 |
| Olefins | 0 | 0 | 2 | 0 |

The results indicate that increasing the metal loading (catalyst of Example 2) increases the activity somewhat but at the expense of decreased ethane selectivity (percent ethane in organic products).

EXAMPLE 7

A Cu/Zn/ZSM-5 catalyst was made by impregnating the 70:1 silica:alumina ZSM-5 used in Examples 1-3 with copper and zinc nitrates dissolved in liquid ammonia, using the procedure described for Examples 1-3. The final catalyst had the composition $Cu_{0.5}Zn$ ZSM-5 ($Cu:Zn:Al_{Fr}=0.5:1:1$; $Al_{Fr}=$Framework (structural) aluminum of zeolite). The catalyst was then evaluated for syngas conversion using a 2:1 hydrogen:carbon monoxide synthesis gas at a pressure of 10170 kPa (1460 psig). The conditions used and the results obtained are shown in Table 4 below.

TABLE 4

| Cu/Zn/ZSM-5 Catalyst | |
|---|---|
| TOS, days | 2.0 |
| Temperature, °C. | 400 |
| Conversion, % | |
| $H_2$ | 20 |
| CO | 43 |
| Selectivity, Wt. % of organics | |
| $CH_4$ | 23 |
| $C_2H_6$ | 70 |
| $C_3H_8$ | 2 |
| $C_4H_{10}$ | 4 |
| $C_5H_{12}$ | 1 |
| Olefins | 0 |

Compared to the CrZnAlZSM-5 catalyst of Example 1, the activity is increased somewhat, at the expense of a decrease, in ethane selectivity.

EXAMPLE 8

The effect of using a non-acidic catalyst was investigated by using the catalysts of Examples 1 (acidic, alpha=900) and 4 (non acidic) in the conversion of the 2:1 hydrogen:carbon monoxide syngas at 500 GHSV, 400° C. and 100 Atm (9800 kPa). The results are shown in Table 4 below.

TABLE 5

| Effect of Zeolite Acid Function | | |
|---|---|---|
| Catalyst | Ex. 1 | Ex. 4 |
| Alpha | 900 | — |
| Conversion, % | | |
| $H_2$ | 12 | 5 |
| CO | 27 | 15 |
| Selectivity (% Organics) | | |
| Methane | 10 | 9 |
| Ethane | 83 | 3 |
| Propane | 4 | 1 |
| Butanes | 3 | 0 |
| Pentanes | 0 | 0 |
| Methanol | 0 | 8 |
| DME | 0 | 79 |

The results in Table 5 above indicate that acidic functionality in the zeolite is necessary for the production of the saturated aliphatics such as ethane.

EXAMPLE 9

The CrZnAlZSM-5 catalyst of Example 1 was compared with three other catalyst of which two were metal impregnated catalysts prepared by the same method and having compositions equivalent to $Cr_{0.5}Zn$ Al ZSM-5 (CR:Zn:Al:$Al_{Fr}$=0.5:1:1:1) and ZnZSM-5 (Zn:$Al_{Fr}$=1:1). The third catalyst was the unimpregnated zeolite having the same silica:alumina ratio of 70:1. The catalysts were evaluated for syngas conversion (2:1 $H_2$:CO) at 370° C., 100 Atm., 500 GHSV. The results are shown in Table 6 below.

TABLE 6

| Effect of Metal Component | | |
|---|---|---|
| Catalyst | CO Conversion, % | Ethane Selectivity |
| CrZnAl ZSM-5 (Ex. 1) | 15 | 81 |
| $Cr_{0.5}$ZnAl ZSM-5 | 17-25 | 71-86 |
| Zn ZSM-5 | 9-12 | 60-67* |
| ZSM-5 | less than 0.5 | 20-25 |

Note:
*Includes ethylene

EXAMPLE 10

The effect of using different zeolites was shown by preparing metal impregnated catalysts by the procedure of Examples 1-3, but using zeolites beta, erionite and ZSM-34. The metal ratios used were 1:1:1:1 (CR:Zn:Al:$Al_{Fr}$) for all the catalysts except for the erionite based catalyst which lacked the impregnated aluminum. The catalysts were then used for syngas conversion (2:1 $H_2$:CO) at 370° C., 100 Atm., 500 GHSV. The results are shown in Table 7 below together with those of the catalyst of Example 1 for comparison.

TABLE 7

| Effect of Zeolite Component | | |
|---|---|---|
| Catalyst | CO Conversion, % | Ethane Selectivity |
| CrZnAl ZSM-5 (Ex. 1) | 15 | 81 |
| CrZnAl Beta | 18-24 | 75-81 |
| CrZnAl ZSM-34 | 23-41 | 19-33 |
| CrZn Erionite | 32-41 | 38 |

The results in Table 7 above show that good conversion and selectivity may be obtained with zeolite beta as well as with ZSM-5. Somewhat lower selectivity is obtained with the small pore zeolites ZSM-34 and erionite.

EXAMPLE 11

For comparative purposes, a physical mixture of the 70:1 silica:alumina zeolite (as the extrudate) and the metal oxides was made by grinding the extrudate with the oxides of chromium, zinc and aluminum in a mortar and pestle. The composition of the mixture was adjusted to be equivalent to that of the catalyst of Example 1. The mixture was used for the conversion of the 2:1 hydrogen:carbon monoxide at 345° C., 500 GHSV, 100 Atm. (9800 kPa). The results are shown in Table 5 below together with the results obtained with the catalyst of Example 1 under the same conditions.

TABLE 5

| Catalyst: | Ex. 1 | Mixture |
|---|---|---|
| Conversion, % | | |
| $H_2$ | 4 | 5 |
| CO | 11 | 14 |
| Selectivity (% organics) | | |
| Methane | 5 | 7 |
| Ethane | 83 | 28 |
| Propane | 7 | 46 |
| Butanes | 5 | 16 |
| Pentanes | 0 | 3 |

Effect of Function Intimacy

The results in Table 5 above indicate that the metal function is to be closely allied to the acidic zeolite function for the desired selectivity for ethane.

We claim:

1. A method of converting a synthesis gas mixture comprising hydrogen and carbon monoxide to a hydrocarbon product, with improved selectivity for the production of ethane, which comprises contacting the synthesis gas under conversion conditions with a conversion catalyst comprising a crystalline zeolite component having acidic functionality and a metal component distributed within the pore structure of the zeolite wherein said metal component comprises a metal or metals which are an effective catalyst for the conversion of synthesis gas to methanol, said conversion catalyst being produced by impregnating the zeolite with an ammoniacal solution of a precursor or precursors of the metal component.

2. A method according to claim 1 in which the metal component comprises the metals chromium, zinc and aluminum.

3. A method according to claim 2 in which the atomic ratios of the metals of the metal component are 0.1 to 10:0.1 to 10:0.1 to 10, respectively.

4. A method according to claim 3 in which the atomic ratios of the metals of the metal component with respect to the aluminum content of the zeolite are 0.1 to 10:0.1 to 10:0.1 to 10:1, respectively.

5. A method according to claim 1 in which the metal component comprises the metals chromium, zinc, aluminum and potassium.

6. A method according to claim 5 in which the atomic ratios of the metals of the metal components are 0.1 to 10:0.1 to 10:0 to 10, respectively.

7. A method according to claim 6 in which the atomic ratios of the metals of the metal component with respect to the aluminum content of the zeolite are 0.1 to 10:0.1 to 10:0 to 10:1, respectively.

8. A method according to claim 1 in which the zeolite component comprises a crystalline aluminosilicate zeolite having a Constraint Index of 1 to 12 and a silica:alumina ratio of at least 12:1.

9. A method according to claim 8 in which the zeolite is ZSM-5.

10. A method according to claim 1 in which the zeolite component comprises zeolite beta.

11. A method of converting a synthesis gas mixture comprising hydrogen and carbon monoxide to a hydrocarbon product, with improved selectivity for the production of ethane, which comprises contacting the synthesis gas under conversion conditions with a conversion catalyst comprising a crystalline zeolite component having acidic functionality and a metal component impregnated into the zeolite from a liquid ammonia solution wherein said metal component comprises a metal or metals which are an effective catalyst for the conversion of synthesis gas to methanol.

12. A method according to claim 11 in which the metal component comprises chromium, zinc and aluminum.

13. A method according to claim 12 in which the atomic ratios of the metals of the metal component are 0.1 to 10:0.1 to 10:0.1 to 10, respectively.

14. A method according to claim 12 in which the atomic ratios of the metals of the metal component with respect to the aluminum content of the zeolite are 0.1 to 10:0.1 to 10:0.1 to 10:1, respectively.

15. A method according to claim 11 in which the metal component comprises the metals chromium, zinc, aluminum and potassium.

16. A method according to claim 15 in which the atomic ratios of the metals of the metal components are 0.1 to 10:0.1 to 10:0.1 to to 10:0 to 10, respectively.

17. A method according to claim 15 in which the atomic ratios of the metals of the metal component with respect to the aluminum content of the zeolite are 0.1 to 10:0.1 to 10:0.1 to 10:0 to 10:1, respectively.

18. A method according to claim 11 in which the zeolite component comprises a crystalline aluminosilicate zeolite having a Constraint Index of 1 to 12 and a silica:alumina ratio of at least 12:1.

19. A method according to claim 18 in which the zeolite is ZSM-5.

20. A method according to claim 11 in which the zeolite component comprises zeolite beta.

21. A method of converting a synthesis gas mixture comprising hydrogen and carbon monoxide to a hydrocarbon product, with improved selectivity for the production of ethane, which comprises contacting the synthesis gas under conversion conditions with a conversion catalyst comprising a crystalline zeolite component having acidic functionality and a metal component of the metals chromium, zinc and aluminum, said conversion catalyst being produced by impregnating the zeolite with an ammoniacal solution of a precursor or precursors of the metal component.

22. A method according to claim 21 in which the atomic ratios of the metals of the metal component are 0.1 to 10:0.1 to 10:0.1 to 10, respectively.

23. A method according to claim 21 in which the metal component comprises chromium, zinc, aluminum and potassium.

24. A method according to claim 5 in which the atomic ratios of the metals of the metal components are 0.1 to 10:0.1 to 10:0.1 to to 10:0 to 10, respectively.

25. A method according to claim 21 in which the zeolite component comprises a crystalline aluminosilicate zeolite having a Constraint Index of 1 to 12 and a silica:alumina ratio of at least 12:1.

26. A method according to claim 25 in which the zeolite is ZSM-5.

27. A method according to claim 21 in which the zeolite component is zeolite beta.

* * * * *